United States Patent
Boehm et al.

(10) Patent No.: US 9,662,180 B2
(45) Date of Patent: May 30, 2017

(54) DEVICE FOR DISPENSING A DENTAL MATERIAL WITH LOCKING MECHANISM

(71) Applicant: 3M INNOVATIVE PROPERTIES COMPANY, St. Paul, MN (US)

(72) Inventors: Andreas J. Boehm, Reichling (DE); Christian A. Richter, Feldafing (DE)

(*) Notice: Subject to any disclaimer, the term of this patent is extended or adjusted under 35 U.S.C. 154(b) by 0 days.

(21) Appl. No.: 14/652,404

(22) PCT Filed: Dec. 10, 2013

(86) PCT No.: PCT/US2013/074107
§ 371 (c)(1),
(2) Date: Jun. 15, 2015

(87) PCT Pub. No.: WO2014/099490
PCT Pub. Date: Jun. 26, 2014

(65) Prior Publication Data
US 2015/0327952 A1    Nov. 19, 2015

(30) Foreign Application Priority Data
Dec. 17, 2012   (EP) ..................... 12197569

(51) Int. Cl.
*A61C 3/00* (2006.01)
*A61C 1/14* (2006.01)
(Continued)

(52) U.S. Cl.
CPC .............. *A61C 1/141* (2013.01); *A61C 1/087* (2013.01); *A61C 1/12* (2013.01); *A61C 3/025* (2013.01);
(Continued)

(58) Field of Classification Search
CPC .......... A61C 1/141; A61C 1/087; A61C 3/025; A61C 17/02; A61C 17/0202; A61C 1/12
(Continued)

(56) References Cited

U.S. PATENT DOCUMENTS 2,529,004 A   11/1950   Eley
3,939,599 A   2/1976    Henry
(Continued)

FOREIGN PATENT DOCUMENTS

CA   1225262   8/1987
CH   656524    7/1986
(Continued)

OTHER PUBLICATIONS

Haffajee, "The effect of SRP on the clinical and microbiological parameters of periodontal diseases," Journal of Clinical Periodontology, 1997, vol. 24, No. 5, pp. 324-334.
(Continued)

*Primary Examiner* — Michael Carey

(57) ABSTRACT

A device for dispensing a dental material includes a nozzle head, a hand piece and a locking mechanism for locking the nozzle head and the hand piece. The locking mechanism includes a snap connection and a screw connection. The locking mechanism is operable between a locked position in which the snap connection is engaged for retaining the nozzle head and the hand piece with each other and in which the screw connection is disengaged; and a secured position in which the snap connection is disengaged and in which the screw connection is engaged for retaining the nozzle head and the hand piece with each other; and a released position in which the snap connection and the screw connection are disengaged.

9 Claims, 6 Drawing Sheets

(51) Int. Cl.
*A61C 3/025* (2006.01)
*A61C 1/08* (2006.01)
*A61C 1/12* (2006.01)
*A61C 17/02* (2006.01)

(52) U.S. Cl.
CPC .......... *A61C 17/02* (2013.01); *A61C 17/0202* (2013.01); *F04C 2270/0421* (2013.01)

(58) Field of Classification Search
USPC ........................................ 433/88, 82, 87, 89
See application file for complete search history.

(56) References Cited

U.S. PATENT DOCUMENTS

| | | | |
|---|---|---|---|
| 3,972,123 | A | 8/1976 | Black |
| 4,078,558 | A | 3/1978 | Woog |
| 4,184,258 | A | 1/1980 | Barrington |
| 4,248,589 | A | 2/1981 | Lewis |
| 4,266,535 | A | 5/1981 | Moret |
| 4,492,575 | A | 1/1985 | Mabille |
| 4,595,365 | A | 6/1986 | Edel |
| 4,676,749 | A | 6/1987 | Mabille |
| 5,120,219 | A | 6/1992 | De Farcy |
| 5,158,455 | A | 10/1992 | Bailey |
| 5,306,144 | A | 4/1994 | Hibst |
| 5,833,456 | A * | 11/1998 | Davis ............... A61C 17/02 433/29 |
| 5,857,851 | A | 1/1999 | Chavanne |
| 6,054,119 | A | 4/2000 | Hurme |
| 6,126,444 | A | 10/2000 | Horiguchi |
| 6,238,211 | B1 * | 5/2001 | Esrock ............... A61C 17/0202 433/80 |
| 6,293,856 | B1 | 9/2001 | Hertz |
| 6,485,304 | B2 | 11/2002 | Beerstecher |
| 6,648,644 | B1 | 11/2003 | Flemmig |
| 6,884,070 | B2 | 4/2005 | Cevey |
| 7,083,411 | B2 | 8/2006 | Flemmig |
| 7,175,430 | B1 | 2/2007 | Gasser |
| 7,762,812 | B2 | 7/2010 | Pichat |
| 7,980,923 | B2 | 7/2011 | Olmo |
| 8,210,846 | B2 | 7/2012 | Duineveld |
| 2001/0021496 | A1 | 9/2001 | Aumuller |
| 2002/0123020 | A1 | 9/2002 | Aumuller |
| 2002/0127513 | A1 | 9/2002 | Bachmann |
| 2003/0008263 | A1 | 1/2003 | Cook |
| 2003/0129560 | A1 | 7/2003 | Atkin |
| 2004/0166474 | A1 | 8/2004 | Gugel |
| 2006/0121411 | A1 | 6/2006 | Wiek |
| 2008/0073350 | A1 * | 3/2008 | Clarot ............... A61C 17/02 220/361 |
| 2009/0317758 | A1 * | 12/2009 | Duineveld ........ A61C 17/0202 433/85 |
| 2010/0029757 | A1 | 2/2010 | Hellerbrand |
| 2010/0151413 | A1 | 6/2010 | Andersson |
| 2010/0297576 | A1 | 11/2010 | Donnet |
| 2011/0117523 | A1 | 5/2011 | Cook |
| 2011/0281238 | A1 | 11/2011 | Cook |
| 2013/0078597 | A1 * | 3/2013 | Thorp ............... A61C 17/0202 433/80 |

FOREIGN PATENT DOCUMENTS

| | | |
|---|---|---|
| CN | 2032047 | 2/1989 |
| CN | 2321545 | 6/1999 |
| CN | 2440591 | 8/2001 |
| DE | 3538324 | 5/1986 |
| DE | 4123019 | 1/1993 |
| EP | 0097288 | 1/1984 |
| EP | 0119021 | 9/1984 |
| EP | 0119735 | 9/1984 |
| EP | 0163610 | 12/1985 |
| EP | 0299229 | 1/1989 |
| EP | 1145689 | 10/2001 |
| EP | 1468659 | 10/2004 |
| EP | 2070505 | 6/2009 |
| ES | 8800833 | 2/1988 |
| FR | 2575062 | 6/1986 |
| FR | 2583630 | 12/1986 |
| FR | 2588182 | 4/1987 |
| FR | 2599244 | 12/1987 |
| GB | 1211150 | 11/1970 |
| GB | 1480594 | 7/1977 |
| GB | 2026359 | 2/1980 |
| JP | 58041550 | 3/1983 |
| JP | 11104148 | 4/1999 |
| JP | 2000-051235 | 2/2000 |
| JP | 2000-083966 | 3/2000 |
| JP | 2001-204741 | 7/2001 |
| JP | 2002-153490 | 5/2002 |
| JP | 2002-165806 | 6/2002 |
| JP | 2002-209911 | 7/2002 |
| JP | 2003-116880 | 4/2003 |
| KR | 20100008362 | 8/2010 |
| WO | WO 89-07932 | 9/1989 |
| WO | WO 94-00078 | 1/1994 |
| WO | WO 96-12447 | 5/1996 |
| WO | WO 97-04741 | 2/1997 |
| WO | WO 98-08906 | 3/1998 |
| WO | WO 99-20197 | 4/1999 |
| WO | WO 00-53154 | 9/2000 |
| WO | WO 01-36159 | 5/2001 |
| WO | WO 01-72273 | 10/2001 |
| WO | WO 02-13721 | 2/2002 |
| WO | WO 02-074180 | 9/2002 |
| WO | WO 03-003934 | 1/2003 |
| WO | WO 03-011164 | 2/2003 |
| WO | WO 03-043519 | 5/2003 |
| WO | WO 03-075784 | 9/2003 |
| WO | WO 2004-075770 | 9/2004 |
| WO | WO 2005-007008 | 1/2005 |
| WO | WO 2005-106734 | 11/2005 |
| WO | WO 2005-115645 | 12/2005 |
| WO | WO 2007-034612 | 3/2007 |
| WO | WO 2007-134336 | 11/2007 |
| WO | WO 2009-148907 | 12/2009 |
| WO | WO 2010-010360 | 1/2010 |
| WO | WO 2011-123123 | 10/2011 |
| WO | WO 2013-191903 | 12/2013 |
| WO | WO 2014-099495 | 6/2014 |
| WO | WO 2014-099800 | 6/2014 |

OTHER PUBLICATIONS

Axelsson, "The significance of maintenance care in the treatment of periodontal disease," Journal of Clinical Periodontology, 1981, vol. 8, No. 4, pp. 281-294.
Zappa, "Root Substance Removal by Scaling and Root Planing" Journal of Periodontology, Dec. 1991, vol. 62, No. 12, pp. 750-754.
Flemmig,"Working Parameters of a Magnetostrictive Ultrasonic Seale Influencing Root Substance Removal In Vitro," Journal of Periodontology 1998, vol. 69, pp. 547-553.
Boyde, Airpolishing Effects on Enamel, Dentine, Cement and Bone, British Dental Journal, Apr. 21, 1984, vol. 156, pp. 287-291.
Sauro, "Dentine desensitization induced by prophylactic and air-polishing procedures: An in vitro dentine permeability and confocal microscopy study," Journal of Dentistry 2010, vol. 38, pp. 411-422.
International Search Report for PCT International Application No. PCT/US2013/074107, mailed on Jul. 2, 2014, 6 pages.

* cited by examiner

DEVICE FOR DISPENSING A DENTAL MATERIAL WITH LOCKING MECHANISM

FIELD OF THE INVENTION

The present invention relates to a device for use in applying a dental material to a desired location, for example the tooth structure of a patient, and more particularly to a powder jet device.

BACKGROUND ART

In dentistry powder jet devices are currently used for applying a fluid stream of abrasive particles, air and water to the tooth structure of a patient, for example for cleaning or pretreating the tooth surfaces.

Generally, a powder jet device may comprise a nozzle head through which the fluid stream can be delivered. Typically the fluid stream contains powder particles which are dispersed and entrained by an air stream guided through a powder containing chamber, and a liquid optionally added to the air/powder mixture, for example through a separate nozzle. In a device of that type used for cleaning tooth surfaces the powder material often comprises dental abrasive particles, and the liquid is normally water.

Examples of powder jet devices for use in the field of dentistry are described in U.S. Pat. No. 4,676,749 (Mabille) or U.S. Pat. No. 5,857,851 (Chavanne). The nozzle head of the device of U.S. Pat. No. 4,676,749 (Mabille) is screwed to the hand piece. The nozzle head of U.S. Pat. No. 5,857,851 (Chavanne) is locked to the hand piece by means of a single snap ring retention. Alternatively, a bayonet mechanism may be used.

Although known devices provide a variety of advantages there is still a desire for a device which is easy to use, which is relatively inexpensive but meets safety expectations of users and hygiene standards, for example as established in dentists' offices.

SUMMARY OF THE INVENTION

The present invention provides a device for dispensing a dental material comprising a nozzle head, a hand piece and a locking mechanism for locking the nozzle head and the hand piece. The locking mechanism comprises a snap connection and a screw connection. The locking mechanism is operable between:
(i) a locked position in which the snap connection is engaged for retaining the nozzle head and the hand piece with each other and in which the screw connection is disengaged;
(ii) a secured position in which the snap connection is disengaged and in which the screw connection is engaged for retaining the nozzle head and the hand piece with each other; and
(iii) a released position in which the snap connection and the screw connection are disengaged.

According to this embodiment of the present invention, the nozzle head and the hand piece may be safely connected to one another by means of the locking mechanism such that an unwanted disengagement of the nozzle head is reliably prevented by means of the locking mechanism at least in the secured position.

The locking mechanism is preferably adapted to allow a rotation of the retained nozzle head relative to the hand piece. In particular the locking mechanism preferably allows a free rotation nozzle head relative to the hand piece which does not cause unlocking of the nozzle head. According to this embodiment of the present invention, the nozzle head and the hand piece are rotatable to one another in the locked position and/or the secured position, wherein an unwanted disengagement of the nozzle head is reliably prevented by means of the locking mechanism in the secured position.

The snap connection may comprise a retaining device for axially retaining the nozzle head at the hand piece. Further the screw connection may comprise a stopper element for preventing a separation of the nozzle head from the hand piece. According to this embodiment of the present invention, the safe connection of the nozzle head and the hand piece is further improved by means of the retaining device and the stopper element.

The retaining device may comprise a ring shaped protrusion arranged at the hand piece and a ring shaped depression or groove arranged at or within the nozzle head. The protrusion and the depression are preferably adapted to engage with each other in the locked position. According to this embodiment of the present invention, the nozzle head may be safely retained at the hand piece by means of the protrusion and the depression. Any disengagement of the ring shaped protrusion from the ring shaped depression requires a certain force in order to pull the ring shaped protrusion out off the ring shaped depression. The manufacturer of the device may adjust the force by selecting a certain material and/or size for the ring shaped protrusion.

The stopper element may comprise a first thread arranged at the nozzle head and at least one pin or at least one second thread arranged at the hand piece. Further the stopper element may comprise a bayonet mechanism. The first thread and the pin or the second thread are preferably engaged for retaining the nozzle head and the hand piece with each other in the secured position. According to this embodiment of the present invention, an unwanted disengagement of the nozzle head from the hand piece is further reliably prevented by means of the first thread and the pin or the second thread.

The nozzle head may extend along a first longitudinal axis. The first thread may comprise at least one ridge for guiding the pin or the second thread from the released position into or toward the locked position or the secured position. The ridge may extend in a circumferential direction around the first longitudinal axis and may be inclined with respect to the first longitudinal axis at a predetermined angle, for example such that the ridge extends along a cylindrically extending helix or screw line. According to this embodiment of the present invention, a movement of the pin or second thread and the first thread relative to one another when moving from the released position into or toward the locked position or the secured position comprises an axial movement component and a rotational movement component. This further improves the effect of preventing an unwanted disengagement of the nozzle head from the hand piece because the device is adapted such that a reverse movement without manual guiding is preferably prevented. This means, a disengagement of the nozzle head from the hand piece has to be carried out by the operator of the dispensing device.

The predetermined angle may be in a range of 60 degrees to 80 degrees. Alternatively, the predetermined angle may be 90 degrees. These ranges for the predetermined angle provide an optimized combination of an axial component and a rotational component for the movement of the pin or second thread and the first thread relative to one another when moving from the released position into the locked position or the secured position.

The ridge may be formed as a rectangular or triangular ridge. The geometric design "rectangular" or "triangular" refers to a cross-section for the ridge in a plane transverse to the dimension along it extends with that cross-section.

The present invention further provides a nozzle head for a device for dispensing a dental material, comprising a nozzle head body comprising a first end at which a nozzle outlet is arranged and a second end. A first thread and a ring shaped depression or groove are formed adjacent the second end. This embodiment of the present invention provides a nozzle head that may be rotatably and safely connected to a hand piece of the dispensing device.

The nozzle head may extend along a first longitudinal axis. The first thread may comprise at least one ridge, wherein the ridge may extend in a circumferential direction around the first longitudinal axis and may be inclined with respect to the first longitudinal axis at a predetermined angle, for example such that the ridge extends along a spiral or screw line. According to this embodiment of the present invention, the nozzle head is designed such that a movement of the first thread relative to a pin or a second thread of a hand piece when moving the nozzle head relative to the hand piece for connecting to one another comprises an axial movement component and a rotational component. This further improves the effect of preventing an unwanted disengagement of the nozzle head from the hand piece. This means, a disengagement of the nozzle head from the hand piece has to be carried out by the operator of the dispensing device.

The nozzle head may comprise a shaft shaped protrusion arranged at the second end, wherein the first thread and the ring shaped depression may be formed at the shaft shaped protrusion such that the first thread is arranged closer to the second end than the ring shaped depression. This facilitates the connection of the nozzle head to the hand piece.

The present invention further provides a hand piece for a device for dispensing a dental material, comprising a front end and a rear end. A fluid supply line is connectable to the rear end. Further at least one pin or a second thread and a ring shaped protrusion are arranged at the front end. This embodiment of the present invention provides a hand piece to which a nozzle head may be rotatably and safely connected.

The at least one pin or the second thread may be arranged closer to the front end than the ring shaped protrusion. This embodiment of the present invention provides a hand piece, wherein a nozzle head has first to engage and pass the pin or second thread before engaging the ring shaped protrusion such that the nozzle head may be first secured at the hand piece before being finally locked thereto. Thus, any unwanted disengagement of the nozzle head from the hand piece before entering the locked position may be reliably prevented.

BRIEF DESCRIPTION OF THE FIGURES

By way of example, a powder jet device having a nozzle head, a hand piece and a locking mechanism in accordance with the present invention will now be described with reference to the accompanying drawings, in which.

DETAILED DESCRIPTION OF THE INVENTION

Figure 1:
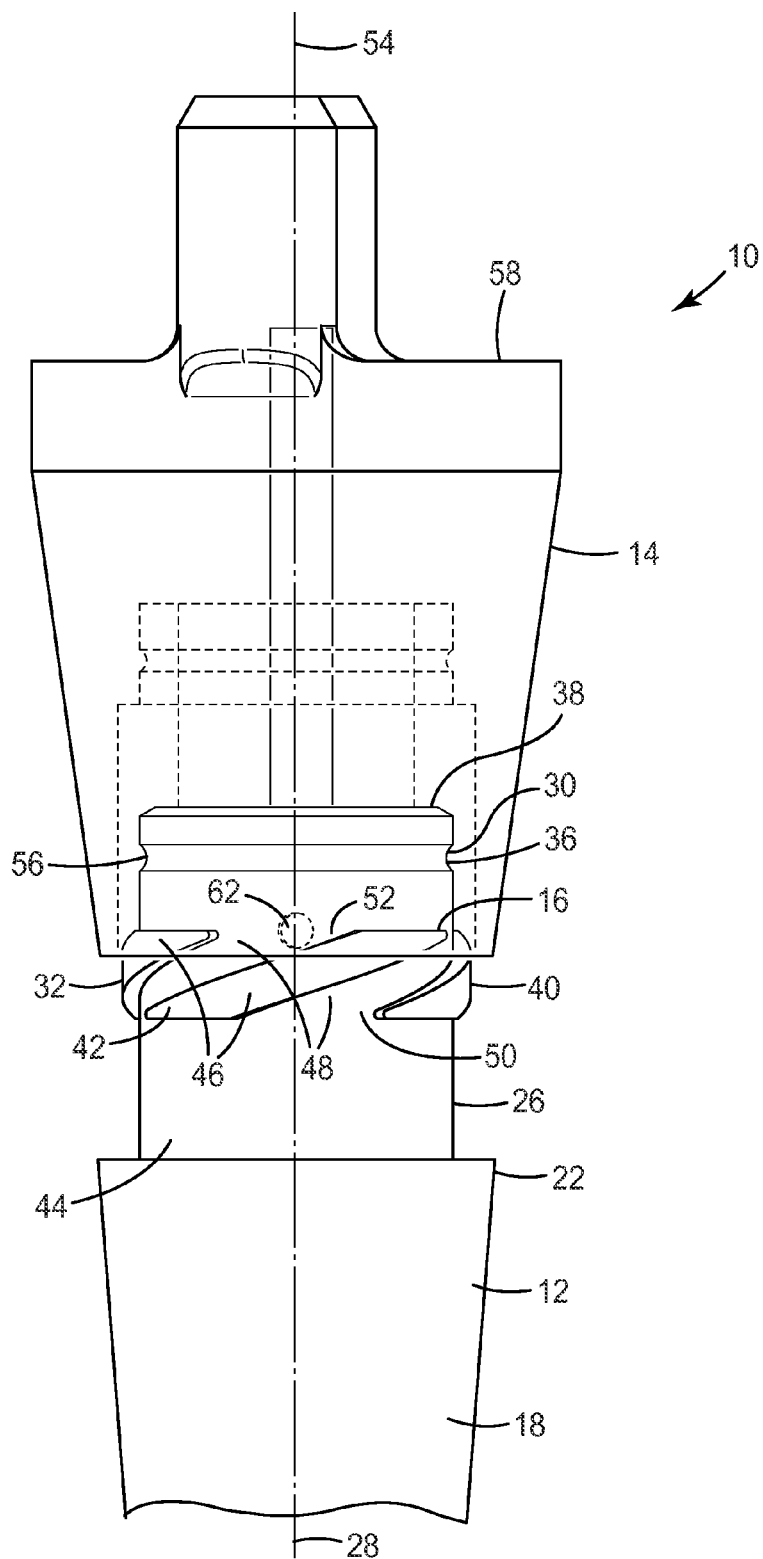
FIG. 1 is a perspective view of a powder jet device according to a first embodiment of the present invention.

The device 10 shown in the drawings is a powder jet device of a type for use in the dental field for applying a powder/gas mixture and a liquid to the tooth structure of a patient.

FIG. 1 shows a perspective view of the powder jet device 10 with the interior thereof according to a first embodiment of the present invention. The powder jet device 10 comprises a nozzle head 12, a hand piece 14, which may also serve or be formed as a handgrip, and a locking mechanism 16. The nozzle head 12 comprises a nozzle head body 18 comprising a first end 20 and a second end 22. A nozzle outlet 24 (FIGS. 5 and 6) is located at the first end 20. A shaft shaped protrusion 26 is arranged at the second end 22. The nozzle head 12 extends along a first longitudinal axis 28. Particularly, the shaft shaped protrusion 26 protrudes from the second end 22 such that the shaft shaped protrusion 26 extends along the first longitudinal axis 28. The shaft shaped protrusion 26 comprises a smaller diameter than the remaining nozzle head body 18.

The locking mechanism 16 comprises a snap connection 30 and a screw connection 32 as will be explained in more detail below. The snap connection 30 comprises a retaining device 34 for axially retaining the nozzle head 12 at the hand piece 14. The retaining device 34 comprises a ring shaped depression 36 formed at the shaft shaped protrusion 26 adjacent a leading end 38 thereof, which is spaced apart from the second end 22. The ring shaped depression 36 extends in a circumferential direction around the first longitudinal axis 28.

The screw connection 32 comprises a stopper element 40. The stopper element 40 comprises a first thread 42. The first thread 42 is formed at the shaft shaped protrusion 26. Particularly, the first thread 42 is formed between the ring shaped depression 36 and the second end 22 if seen in a direction of the first longitudinal axis 28. Thus, the first thread 42 is arranged closer to the second end 22 than the ring shaped depression 36. Further, the first thread 42 and the ring shaped depression 36 are formed adjacent the second end 20. On the shaft shaped protrusion 26, a free portion 44 is formed between the first thread 42 and the second end 22 if seen in a direction of the first longitudinal axis 28. A free portion 44 in the sense of the present invention is to be understood as a portion not including any screw pattern. This means, a free portion 44 in the sense of the present invention does not comprise any depressions, recesses, protrusions or the like but a plane surface which may be curved around the first longitudinal axis 28.

The first thread 42 comprises at least one ridge 46. In the embodiment shown in FIG. 1, the first thread 42 comprises four ridges 46 which are equally spaced apart from one another. The ridges 46 extend in a circumferential direction around the first longitudinal axis 28 and are inclined with respect to the first longitudinal axis 28 at a predetermined angle. The predetermined angle may be in a range of 60 degrees to 80 degrees such as 70 degrees. The predetermined angle is defined between the first longitudinal axis 28 and the path of the first thread 42 if seen from the leading end 38 of the shaft shaped protrusion 26 to the second end 22. The ridges 46 are formed as rectangular ridges, i.e. as ridges having a rectangular cross-section. Particularly, the ridges 46 extend parallel to one another in a circumferential direction around the first longitudinal axis 28 and along the first longitudinal axis 28. This means, the ridges 46 may extend along a path having an axial dimension and a circumferential dimension as is known from a thread of a screw. Further, the ridges 46 are formed straight. Thus, the ridges 46 define guiding channels 48 therebetween. Each guiding channel 48 has a first entry 50 and a second entry 52, wherein the first entry 50 is arranged closer to the leading end 38 than the second entry 52. With other words, the first entry 50 faces the leading end 38 of the shaft shaped protrusion 26, whereas the second entry 52 faces the second end 22 of the nozzle head body 18.

Figure 2:
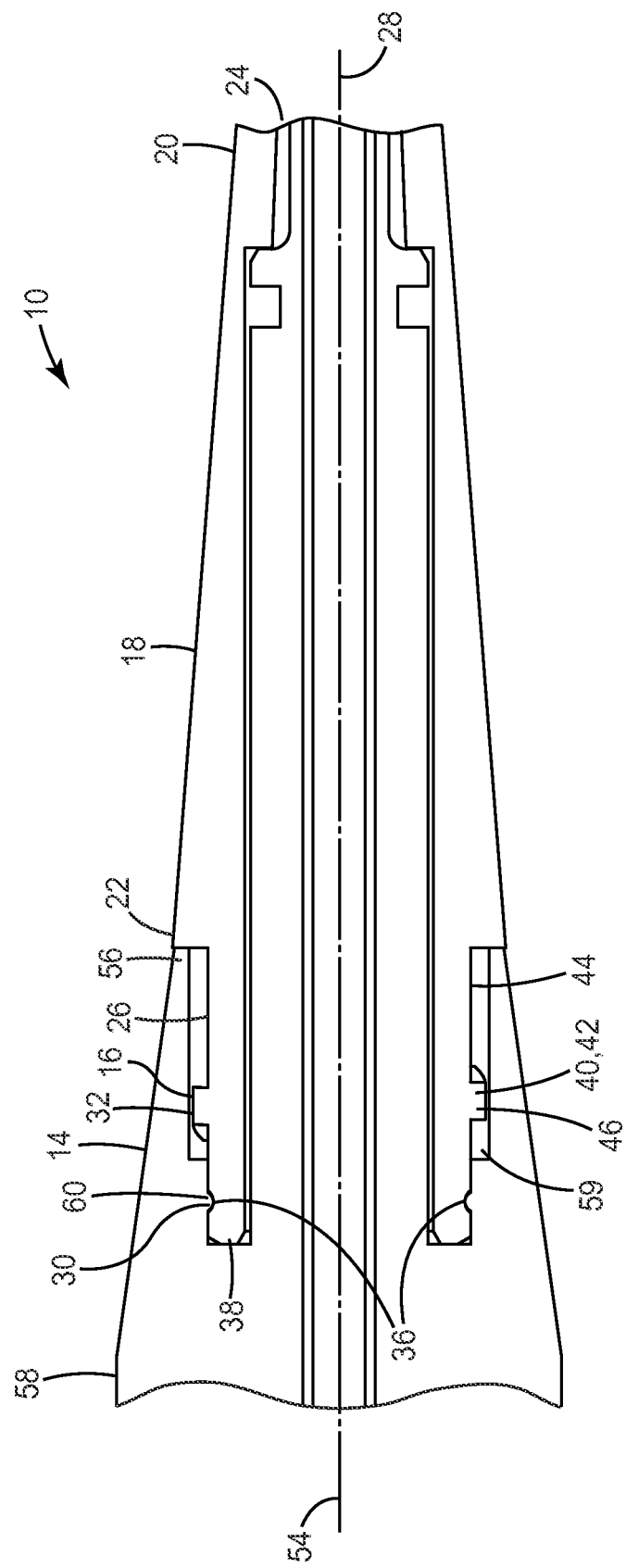
FIG. 2 is a longitudinal section view of the powder jet device.

FIG. 2 is a longitudinal section view of the powder jet device 10. The hand piece 14 is at least partially formed as a hollow tube, which extends along a second longitudinal axis 54. The hand piece 14 comprises a front end 56 and a rear end 58. A fluid supply line (not shown) of a not shown fluid supply source may be connected to the rear end 58. An insertion portion 59 is formed at the front end 56. The insertion portion 59 is adapted to receive the shaft shaped protrusion 26 as will be explained in more detail below. The retaining device 34 comprises a ring shaped protrusion 60. The ring shaped protrusion 60 is formed between the front end 56 and the rear end 58 within the insertion portion 59. More particularly, the ring shaped protrusion 60 is arranged within the insertion portion 59 at a distance from the front end 56. The ring shaped protrusion 60 radially protrudes with respect to the second longitudinal axis 54 from an inner wall of the hand piece 14 within the insertion portion 59. The ring shaped protrusion 60 may extend completely along the inner wall of the hand piece 14 within the insertion portion in a circumferential direction with respect to the second longitudinal axis 54. Alternatively, the ring shaped protrusion 60 may be formed as segments being distributed along the circumferential direction with respect to the second longitudinal axis 54. The ring shaped protrusion 60 is adapted to engage the ring shaped protrusion 36 arranged at the nozzle head 12 such the position of the ring shaped protrusion 60 depends on the position of the ring shaped depression 36 and vice versa, respectively. Thus, the positions of the ring shaped protrusion 60 and the ring shaped depression 36 are not limited to the aforementioned positions. For example, the ring shaped protrusion 60 may also be arranged closer to the front end 56 than to the rear end 58. The stopper element 40 further comprises at least one pin 62. As shown in FIG. 1, the stopper element 40 comprises two pins 62 in this embodiment. The two pins 62 are located side by side with the second longitudinal axis 54 therebetween. Particularly, the pins 62 are arranged at an inner wall of the hand piece 14 within the insertion portion 59 adjacent the front end 56. The pins 62 are arranged closer to the front end 56 than the ring shaped protrusion 60. Alternatively, instead of the pins 62, a second thread may be provided which is adapted to the form of the first thread 42 and vice versa. Thus, the first thread 42 and the second thread may be formed so as to cooperate. The pins 62 may comprise an angular or rounded cross-section.

Figure 3:
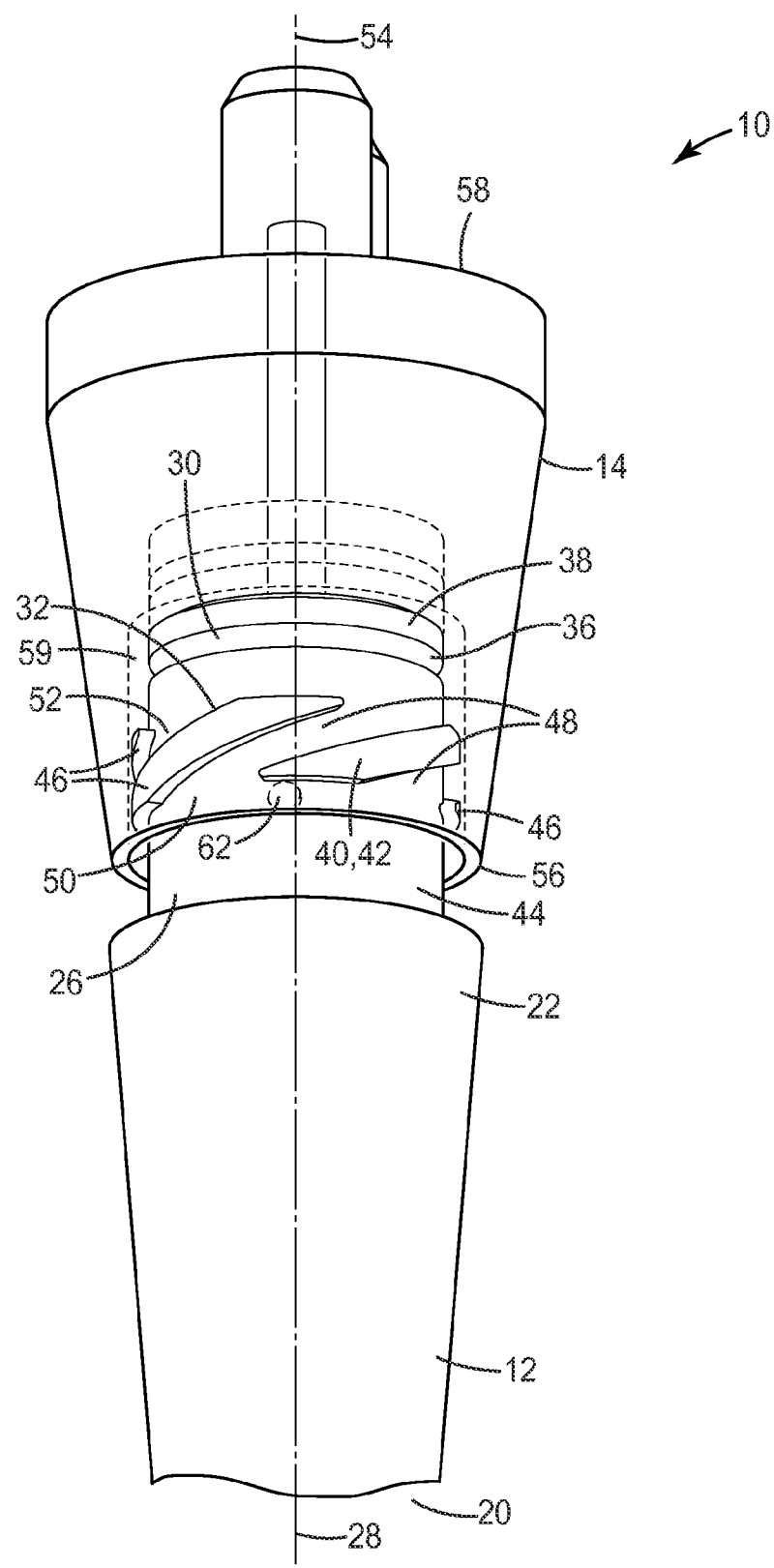
FIG. 3 is a perspective view of a part of the powder jet device with the locking mechanism in the released position.

The operation for connecting and disconnecting the nozzle head 12 and the hand piece 14 will now be explained. At the beginning, the nozzle head 12 and the hand piece 14 are not connected to one another. Thus, the locking mechanism 16 is in a released position, in which the snap connection 30 and the screw connection 32 are disengaged. FIG. 3 is a perspective view of a part of the powder jet device 10 with the interior thereof showing the nozzle head 12, the hand piece 14 and the locking mechanism 16, wherein the locking mechanism 16 is in a released position. In order to connect the nozzle head 12 to the hand piece 14, the nozzle head 12 with the shaft shaped protrusion 26 facing the front end 56 of the hand piece 14 is moved towards the hand piece 14 such that the shaft shaped protrusion 26 is inserted into the insertion portion 59 and each of the pins 62 engages and enters one of the first entries 50 of the guiding channels 48. In this state, the first longitudinal axis 28 and the second longitudinal axis 54 fall together. Then, the nozzle head 12 is rotated around the longitudinal axis 54 of the hand piece 14 and further moved towards the hand piece 14 such that the pins 62 are guided within the guiding channels 48 to the second entries 52. Due to the inclination of the ridges 46, the movement of the pins 62 through the first thread 42 when connecting the nozzle head 12 to the hand piece 14 includes a movement component in a direction of the second longitudinal axis 54 and a movement component in a circumferential direction with respect to the second longitudinal axis 54. After the pins 62 have reached the second entries 52, the pins 62 are capable to exit the guiding channels 48 formed by the ridges 46 of the first thread 42. Subsequently, the nozzle head 12 is moved in an axial direction with respect to the second longitudinal axis 54 of the hand piece 14 such that the pins 62 exit the guiding channels 48 out of the second entries 52 and reach the free portion 44 of the nozzle head 12. Any movement of the nozzle head 12 backwards, i.e. away from the hand piece 14, is now restricted and has to be carried out manually because the first thread 42 prevents the pins 62 from moving back alone through the guiding channels 48 if not completely overlapping with the second entries 52. Thus, the locking mechanism 16 is moved into a secured position in which the snap connection 30 is disengaged and in which the screw connection 32 is engaged for retaining the nozzle head 12 and the hand piece 14 with each other. The nozzle head 12 is then further moved in the axial direction with respect to the second longitudinal axis 54 of the hand piece 14 until the ring shaped protrusion 60 engages the ring shaped depression 36. During this movement, the pins 62 move along the free portion 44. In this state, the nozzle head 12 is retained at the hand piece 14 by means of the cooperation of the ring shaped protrusion 60 and the ring shaped depression 36 so that the locking mechanism 16 is in a locked position.

Figure 4:
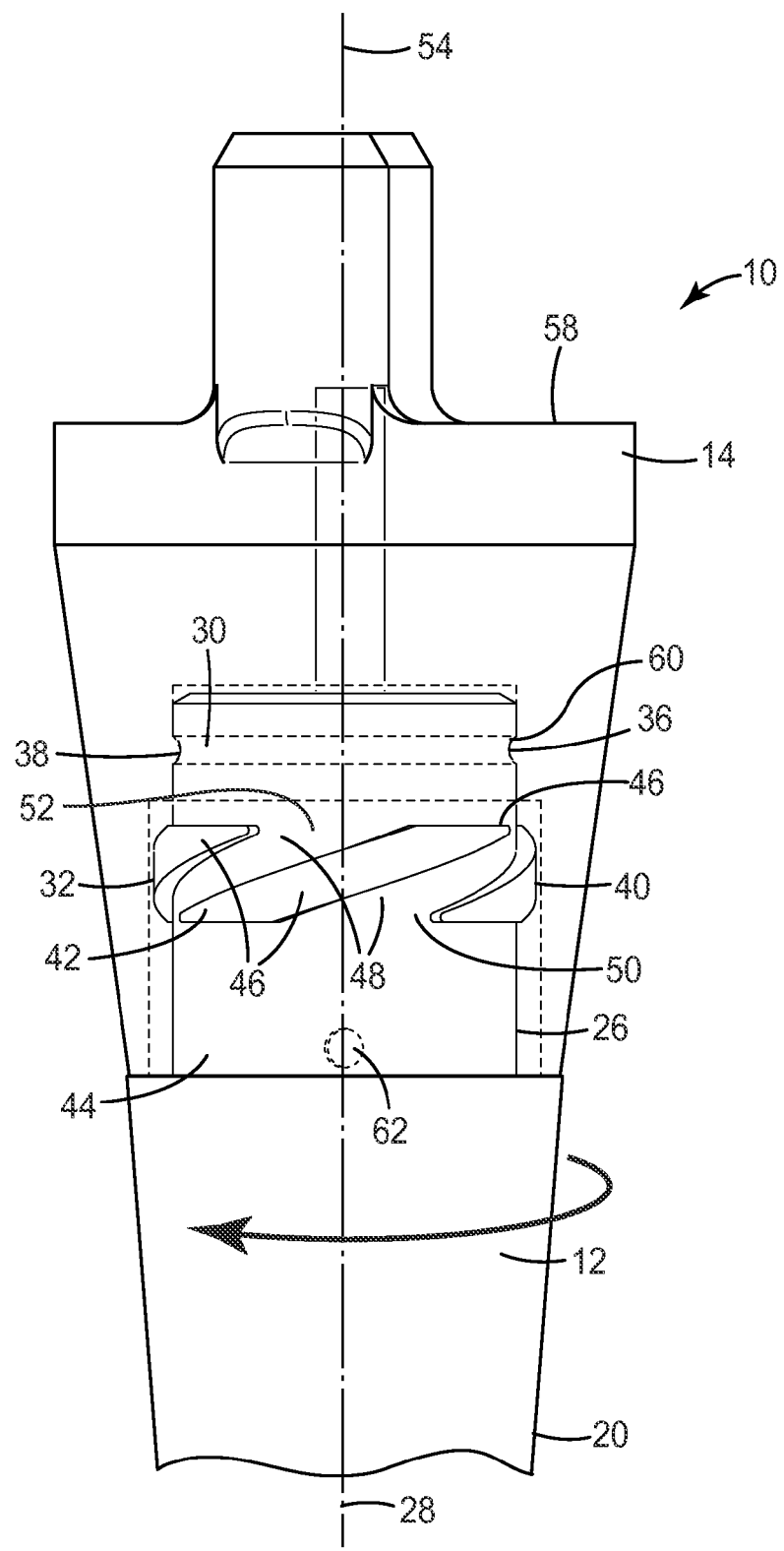
FIG. 4 is a further perspective view of a part of the powder jet device with the locking mechanism in the locked position.

FIG. 4 is a perspective view of a part of the powder jet device 10 with the interior thereof showing the nozzle head 12, the hand piece 14 and the locking mechanism 16, wherein the locking mechanism 16 is in a locked position. As the pins 62 are spaced apart from the first thread 42 in the axial direction, the screw connection 32 is disengaged. In the locked position, the nozzle head 12 is freely turnable or rotatable relative to the hand piece 14 as the ring shaped protrusion 60 is movable within the ring shaped depression 36 in a circumferential direction but not in an axial direction with respect to the second longitudinal axis 54. Further, the pins 62 may move in a circumferential direction as the free portion 44 does not restrict a movement of the pins 62 in a circumferential direction when rotating the nozzle head 12 relative to the hand piece 14 but allows such a movement.

In case of an unwanted loosening of the ring shaped protrusion 60 from the ring shaped depression 36 or if the ring shaped protrusion 58 does not fully engage the ring shaped depression 36, the nozzle head 12 may not fully be disengaged from the hand piece 14 because the inclined ridges 46 prevent the pins 62 from moving back through the guiding channels 48, i.e. in a direction from the second entries 52 towards the first entries 50. Thus, the screw connection 32 comprising the first thread 42 and the pins 62 is engaged in case the ring shaped protrusion 60 does not fully engage the ring shaped depression 36. Thus the locking mechanism 16 is in the secured position.

In order to disengage or remove the nozzle head 12 from the hand piece 14, the ring shaped protrusion 60 is disengaged from the ring shaped depression 36, for example by pulling the nozzle head 12 away from the hand piece 14. Then, the nozzle head 12 has to be rotated in the circumferential direction until the pins 62 overlap with the second entries 52 and may enter the guiding channels 48. Then, the pins 62 are moved through the guiding channels 48 from the second entries 52 to the first entries 50 until the pins 62 exit the guiding channels 48 at the first entries 50. Thus, the locking mechanism 16 is in the released position again and the nozzle head 12 is disconnected from the hand piece 14.

According to the above description, the locking mechanism 16 is operable between:
  (i) a locked position in which the snap connection 30 is engaged for retaining the nozzle head 12 and the hand piece 14 with each other, and in which the screw connection 32 is disengaged;
  (ii) a secured position in which the snap connection 30 is disengaged and in which the screw connection 32 is engaged for retaining the nozzle head 12 and the hand piece 14 with each other; and
  (iii) a released position in which the snap connection 30 and the screw connection 32 are disengaged.

Figure 5:
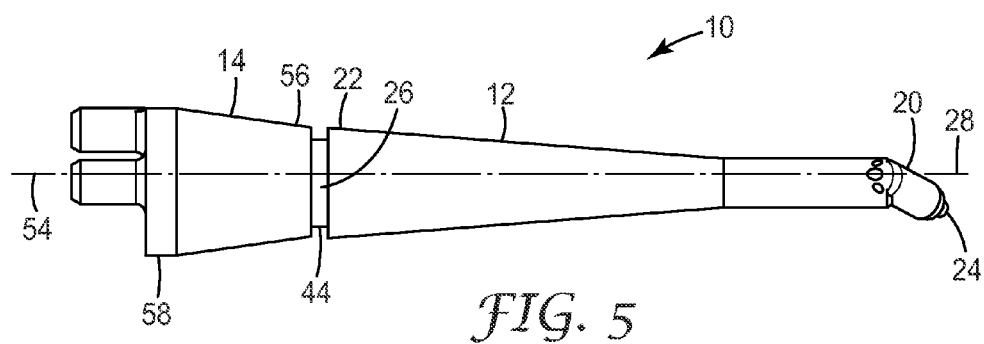
FIG. 5 is a perspective view of a modification of the powder jet device with the locking mechanism in the secured position.

FIG. 5 shows a perspective view of a modification of the powder jet device 10, wherein the nozzle head 12 is not fully connected to the hand piece 14 and the locking mechanism 16 is in the secured position. In this further development of the above embodiment of the present invention, the shaft shaped protrusion 26 of the nozzle head 12 may be colored as shown in FIG. 5. For example, the shaft shaped protrusion 26 may be red or another signal color. Such a color provided on the shaft shaped protrusion 26 helps an operator of the powder jet device 10 to recognize whether the nozzle head 12 is correctly or completely connected to the hand piece 14. In case the nozzle head 12 is not fully connected to the hand piece 14, the locking mechanism 16 is not in the locked position. Therefore, the ring shaped protrusion 58 arranged at the hand piece 14 does not fully engage the ring shaped depression 36 arranged at the nozzle head 12. Accordingly, the second end 22 of the nozzle head 12 is axially spaced apart from the front end 56 of the hand piece 14 as shown in FIG. 5. Thus, the colored ring shaped protrusion 26 may bee seen from outside by the operator and the operator recognizes that the nozzle head 12 is correctly or completely connected to the hand piece 14.

Figure 6:
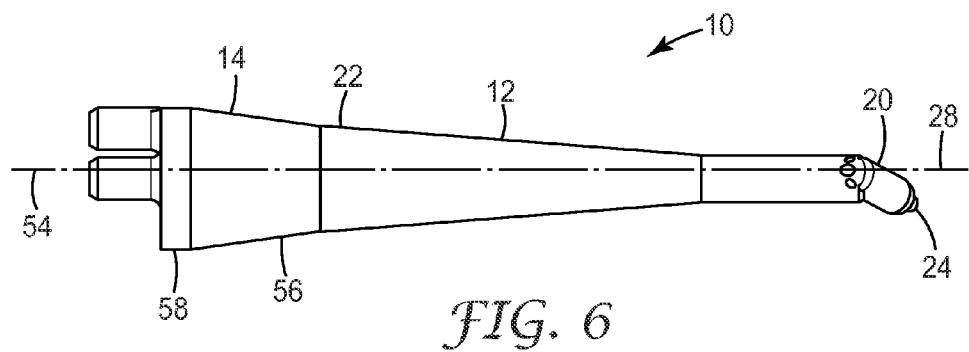
FIG. 6 is a further perspective view of the modification of the powder jet device with the locking mechanism in the locked position.

FIG. 6 is a further perspective view of the modification of the powder jet device 10, wherein the nozzle head 12 is fully connected to the hand piece 14 and the locking mechanism 16 is in the locked position. As shown in FIG. 6, the color on the ring shaped protrusion 26 is only hidden and may not be seen if the nozzle head 12 is correctly or completely connected to the hand piece 14 as then the shaft shaped protrusion 26 is fully inserted into the insertion portion 59 and the ring shaped protrusion 58 arranged at the hand piece 14 engages the ring shaped depression 36 arranged at the nozzle head 12. Accordingly, the second end 22 of the nozzle head 12 is not axially spaced apart from the front end 56 of the hand piece 14.

Figure 7:
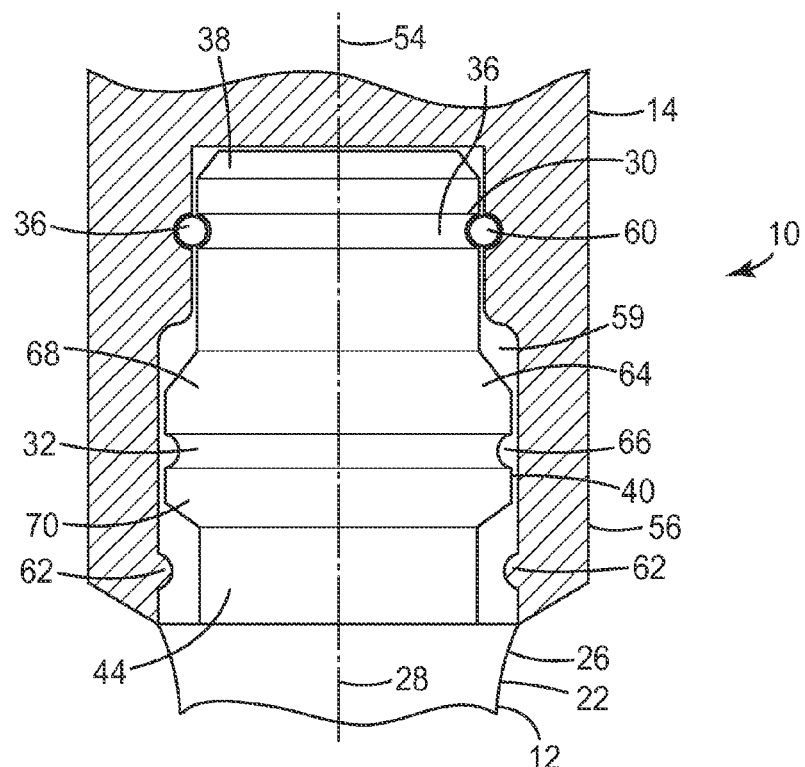
FIG. 7 is a longitudinal section view of a part a powder jet device according to a second embodiment of the present invention.

FIG. 7 shows a longitudinal section view of a part of a powder jet device 10 according to second embodiment of the present invention. Only the differences from the first embodiment will be explained and identical constructional members are indicated by identical reference signs. As shown in FIG. 7, which shows only a part of the connection of the nozzle head 12 to the hand piece 14, the retaining device 34 of the snap connection 30 comprises a ring shaped depression 36 formed at the shaft shaped protrusion 26 adjacent the leading end 38 thereof, which is spaced apart from the second end 22. The ring shaped depression 36 extends in a circumferential direction around the first longitudinal axis 28.

The stopper element 40 of the screw connection 32 does not comprise the first thread 42 but a bead 64 which is formed as a radial extension from the shaft shaped protrusion with respect to the first longitudinal axis 28. The bead 64 comprises a circumferential depression 66 arranged at an axial middle of the bead 64 with respect to the first longitudinal axis 28. The bead 64 further comprises a front portion 68, which is arranged closer to the leading end 38 of the shaft shaped protrusion 26 and the ring shaped depression 36, and a rear portion 70, which is arranged closer to the second end 22 of the nozzle head 12. The circumferential depression 66 is located between the front portion 68 and the rear portion 70.

When connecting the nozzle head 12 to the hand piece 14, the nozzle head 12 with the shaft shaped protrusion 26 facing the front end 56 of the hand piece 14 is moved towards the hand piece 14 such that each of the pins 62 contacts the front portion 68 of the bead 64. Then, the nozzle head 12 is further moved in an axial direction such that the pins 62 are guided over the front portion 68 of the bead 64 and enter the circumferential depression 66. This state corresponds to the secured position of the locking mechanism 16 as the ring shaped protrusion 60 is not engaged with the ring shaped depression 36, i.e. the snap connection 30 is disengaged, but the pins 62 engage the circumferential depression 66 such that the screw connection 32 is engaged. Accordingly, any movement of the nozzle head 12 backwards, i.e. away from the hand piece 14, is now restricted and has to be carried out manually because the rear portion 70 and the circumferential depression 66 into which the pins 62 fit, prevent the pins 62 from moving back unless the nozzle head 12 is pulled away from the hand piece 14 with a certain force. It is to be noted that the pins 62 are elastically deformable to a certain degree in order to be capable to move along the bead 64. Then, the nozzle head 12 has to be further pushed or pressed in the axial direction towards the hand piece 14 with a certain degree of force in order to move the pins 62 out of the circumferential depression 66 and over the rear portion 70 of the bead 64. After the pins 62 have passed the rear portion 70 of the bead 64, the pins 62 reach the free portion 44 of the nozzle head 12. Subsequently, the nozzle head 12 has to be moved a further small distance in the axial direction towards the hand piece 14 until the ring shaped protrusion 60 engages the ring shaped depression 36. This state corresponds to the locked position as the snap connection 30 formed by the ring shaped protrusion 60 and the ring shaped depression 36 is engaged and the screw connection 32 formed by the pins 62 and the bead 64 is disengaged. In the locked position, the nozzle head 12 is freely turnable or rotatable relative to the hand piece 14 as the ring shaped protrusion 60 is movable within the ring shaped depression 36 in a circumferential direction but not in an axial direction with respect to the second longitudinal axis 54. Further, the pins 62 may move in a circumferential direction as the free portion 44 does not restrict a movement of the pins 62 in a circumferential direction when rotating the nozzle head 12 relative to the hand piece 14 but allows such a movement.

Figure 8:
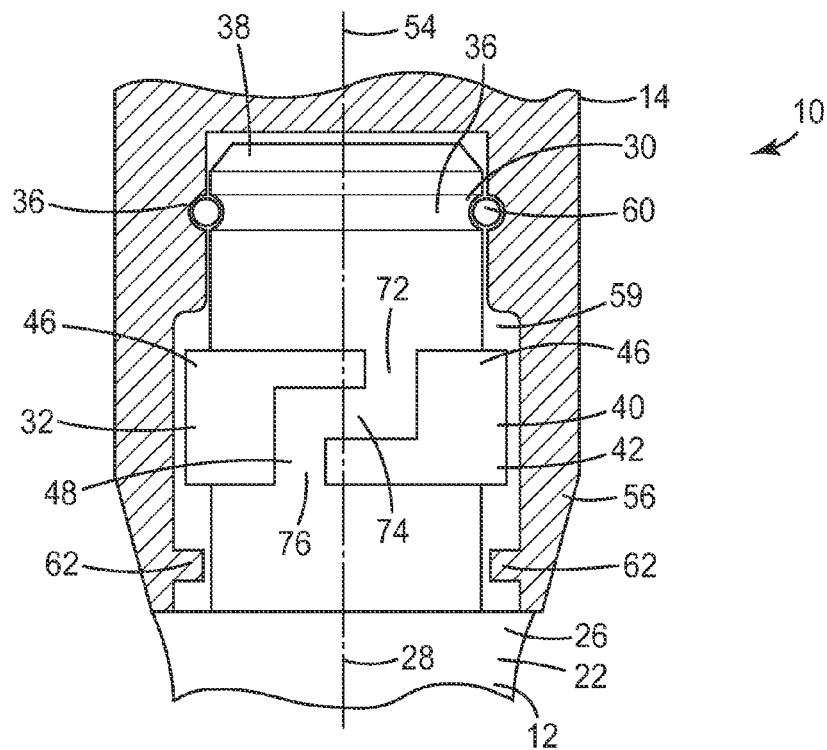
FIG. 8 is a longitudinal section view of a part a powder jet device according to a third embodiment of the present invention.

FIG. 8 shows a longitudinal section view of a part of a powder jet device according to a third embodiment of the present invention. Only the differences from the first embodiment will be explained and identical constructional members are indicated by identical reference signs. As shown in FIG. 8, which shows only a part of the connection of the nozzle head 12 to the hand piece 14, the stopper element 40 of the screw connection 32 comprises the first thread 42 which comprises ridges 46. However, the ridges 46 are not formed straight but in an angled manner. Accordingly, the guiding channels 48 formed between two adjacent ridges 46 are also angled. Thus, the guiding channels 48 comprise a first axial portion 72, a radial portion 74 and a second portion 76 if seen from the leading end 38 of the shaft shaped protrusion 26 to the second end 22 of the nozzle head 12.

In order to connect the nozzle head 12 to the hand piece 14, the pins 62 arranged at the hand piece 14 have to be guided through the guiding channels 48 in that the nozzle head 12 is first moved in an axial direction, wherein the pins 62 move through the first axial portion 72 until reaching the radial portion 74. Then the nozzle head 12 has to be rotated in a circumferential direction, wherein the pins 62 move through the radial portion 72 until reaching the second axial portion 76. If the pins 62 are within the radial portion 72, this state corresponds to the secured position of the locking mechanism 16 as the pins 62 are engaged with the first thread 42. Then, the nozzle head 12 has to be moved in the axial direction through the second axial portion 76 until reaching the free portion 44. Subsequently, the nozzle head 12 has to be moved a further small distance in the axial direction towards the hand piece 14 until the ring shaped protrusion 60 engages the ring shaped depression 36. This state corresponds to the locked position as the snap connection 30 formed by the ring shaped protrusion 60 and the ring shaped depression 36 is engaged and the screw connection 32 formed by the pins 62 and the first thread 42 is disengaged. In the locked position, the nozzle head 12 is freely turnable or rotatable relative to the hand piece 14 as the ring shaped protrusion 60 is movable within the ring shaped depression 36 in a circumferential direction but not in an axial direction with respect to the second longitudinal axis 54. Further, the pins 62 may move in a circumferential direction as the free portion 44 does not restrict a movement of the pins 62 in a circumferential direction when rotating the nozzle head 12 relative to the hand piece 14 but allows such a movement.

What is claimed is:

1. A device for dispensing a dental material comprising a nozzle head, a hand piece and a locking mechanism for locking the nozzle head and the hand piece, wherein the locking mechanism comprises:
   a snap connection and a screw connection;
   the locking mechanism being operable between:
   a locked position in which the snap connection is engaged for retaining the nozzle head and the hand piece with each other and in which the screw connection is disengaged;
   a secured position in which the snap connection is disengaged and in which the screw connection is engaged for retaining the nozzle head and the hand piece with each other; and
   a released position in which the snap connection and the screw connection are disengaged;
   wherein the snap connection comprises a retaining device for axially retaining the nozzle head to the hand piece, and the screw connection comprises a stopper element to prevent separation of the nozzle head from the hand piece;
   wherein the retaining device comprises a ring shaped protrusion on the hand piece and a ring shaped depression on the nozzle head, wherein the ring shaped protrusion engages the ring shaped depression in the locked position; and
   wherein the stopper element comprises a first thread on the nozzle head and at least one pin or at least one second thread on the hand piece, wherein the first thread and the pin or the second thread are engaged to retain the nozzle head and the hand piece with each other in the secured position.

2. The device according to claim 1, wherein the locking mechanism is adapted to allow a rotation of the retained nozzle head relative to the hand piece in the locked position and/or the secured position.

3. The device of claim 1, wherein the nozzle head extends along a first longitudinal axis, wherein the first thread comprises at least one ridge for guiding the pin or second thread from the released position into the locked position or the secured position, wherein the ridge extends in a circumferential direction around the first longitudinal axis and is inclined with respect to the first longitudinal axis at a predetermined angle.

4. The device of claim 3, wherein the predetermined angle is in a range of 60 degrees to 80 degrees.

5. The device according to claim 3, wherein the predetermined angle is 90 degrees.

6. The device of claim 3, wherein the ridge is formed as a rectangular ridge.

7. A powder-jet device for applying to a tooth structure of a patient a dental material comprising a powder/gas mixture and a liquid, the device comprising:
   a nozzle head comprising a nozzle head body extending along a longitudinal axis and comprising a first end at which a nozzle outlet is arranged and a second end comprising a shaft shaped protrusion, wherein the shaft shaped protrusion comprises a thread and a ring shaped depression, and wherein the thread comprises at least one ridge extending in a circumferential direction around the longitudinal axis and inclined with respect to the longitudinal axis at an angle of 60 degrees to 80 degrees; and
   a hand piece comprising a rear end to which a fluid supply line is connectable and a front end, wherein the front end of the hand piece comprises at least one pin and a ring shaped protrusion;
wherein the thread on the second end of the nozzle head engages the at least one pin on the hand piece to form a screw connection to secure the nozzle head to the hand piece while allowing rotation of the nozzle head with respect to the hand piece, and wherein the ring shaped protrusion on the front end of the hand piece engages the ring shaped depression on the second end of the nozzle head to form a snap connection to lock the nozzle head to the hand piece.

8. The powder-jet device of claim 7, wherein the thread is closer to the second end of the nozzle head than the ring shaped depression.

9. The powder-jet device of claim 7, wherein the at least one pin is closer to the front end of the hand piece than the ring shaped protrusion.

* * * * *